United States Patent [19]

Moore

[11] Patent Number: 5,046,363
[45] Date of Patent: Sep. 10, 1991

[54] APPARATUS FOR RAPID NON-DESTRUCTIVE MEASUREMENT OF DIE ATTACH QUALITY IN PACKAGED INTEGRATED CIRCUITS

[75] Inventor: Thomas M. Moore, Dallas, Tex.

[73] Assignee: Texas Instruments Incorporated, Dallas, Tex.

[21] Appl. No.: 423,519

[22] Filed: Oct. 13, 1989

Related U.S. Application Data

[63] Continuation of Ser. No. 172,735, Mar. 23, 1988, abandoned.

[51] Int. Cl.⁵ .............................................. G01N 29/04
[52] U.S. Cl. ........................................ 73/588; 73/599
[58] Field of Search ................ 73/588, 606, 627, 629, 73/599; 324/501

[56] References Cited

PUBLICATIONS

Gilmore et al., "High-Frequency Ultrasonic Testing of Bonds: Application to Silicon Power Devices", Materials Evaluation (Jan. 1979), pp. 65–72.

Primary Examiner—Hezron E. Williams
Assistant Examiner—Rose M. Finley
Attorney, Agent, or Firm—B. Peter Barndt; James T. Comfort; Melvin Sharp

[57] ABSTRACT

A method and apparatus is disclosed for the non-destructive measurement of die-attach quality in packaged integrated circuit. The apparatus is used in a production line and uses acoustical pulses to generate signals from within the integrated circuit indicative of the die-attach quality.

29 Claims, 4 Drawing Sheets

APPARATUS FOR RAPID NON-DESTRUCTIVE MEASUREMENT OF DIE ATTACH QUALITY IN PACKAGED INTEGRATED CIRCUITS

This application is a continuation of application Ser. No. 172,735, now abandoned, filed 3/23/88.

FIELD OF THE INVENTION

The invention relates to semiconductor devices and more particularly to apparatus and method of detecting voids in the die-attach layer of integrated circuit packages and delaminations between the integrated circuit chips and the packaging material in plastic packaged integrated circuits using acoustic waves.

DISCUSSION OF THE PRIOR ART

Innovations in ultrasonic non-destructive evaluation, or NDE, closely followed advances in electronics technology. As the capability of pulse-echo detection electronics improved, large-scale techniques developed in the sea evolved into laboratory ultrasonic NDE devices. The field of ultrasonic NDE was launched by Floyd Firestone, a physicist at the University of Michigan. In 1942, Firestone received a patent on the "Ultrasonic Reflectoscope" which detected voids or cracks inside of manufactured parts by the pulse-echo technique using a contact transducer. Immersion methods were developed soon thereafter. The development of pulse-echo RADAR in 1938 provided the electronics capability for Firestone's Reflectoscope. Firestone's original Reflectoscope operated in the range of 2–25 MHz which provided a wavelength of 0.2–3 mm in steel.

Today's commercial NDE devices are essentially mini-SONAR systems, many of which can also produce an image, and are remarkably similar in principle to the early Reflectoscope.

Although commercial acoustic microscope manufacturers have offered images of the die-attach layer in ceramic-packaged IC's, very little work has been done in capitalizing on this capability until quite recently. In 1986, Raytheon completed a report for the Rome Air Development Center on techniques for imaging die-attach in ceramic-packaged IC's. This report recommends pulse-echo acoustic imaging above all other techniques including x-ray radiography and scanning laser acoustic microscopy (SLAM) due to the contrast and reliability of the pulse-echo image. The report made this recommendation in spite of the noted lack of automation available for this type of evaluation.

The die-attach layer in ceramic-packaged IC's can be imaged with higher frequencies than used for plastic package inspection due to the superior sound transmission in the ceramic material.

The pulse-echo principle of the SONAR system is the basis for the IC package acoustic microscopy. In both systems a sound pulse of short duration is transmitted at a relatively low repetition rate and the time delay before an echo is received is measured.

In the case of SONAR, this delay indicates the distance to the target. And in the reflection SAM, the echo signals are gated in time so that the image can be generated of a plane at a specific depth within the sample.

SUMMARY OF THE INVENTION

The invention is similar to that disclosed and claimed in copending patent application Ser. No. 172,043, filed Mar. 23, 1988, and entitled APPARATUS AND METHOD FOR AUTOMATED NON-DESTRUCTIVE INSPECTION OF INTEGRATED CIRCUIT PACKAGES.

The present invention provides an in-line process control sensor that will report the quality of die attach in a packaged IC averaged over the total die attach area. Instead of a focused probe like that used to form an image of a sub-surface interface in the above referenced copending patent application, the present invention uses a plane wave transducer that insonifies a square field the size of the bar inside the particular package being examined. This size match will exclude reflections from the leads. The data acquisition can result from a single measurement with an immersion transducer that produces a sound field the same size as the bar, or by a contact transducer that produces a similar sound field.

If the bar is larger than the largest available transducer size, a point scan, line scan, or an area scan (where the area is smaller that the bar size) can be integrated over the whole bar to give the same results. A scanned array may also be used.

A plastic packaged integrated circuit is imaged through the top, therefore the integrated circuit package is inverted and makes contact to a permanent delay contact transducer or to water in the use of an immersion transducer. In the case of the permanent delay contact transducer the cross section of the delay medium is the same size and shape as the bar. In the case of a water immersion system, a short water path is established, using a water bath, between the transducer and the package. The transducer can be located above or below the integrated circuit package in the water bath. In the water immersion system, either the transducer is the same size as the bar, or an aperture is placed between the transducer and the sample. The aperture adjusts the size and shape of the transducer sound field to match that of the bar. The aperture material attenuates and/or delays the sound field surrounding the transmitted field.

In the application to plastic packaged integrated circuits, the intensity of the reflection from the package/bar interface is compared with the intensity from the bar/die attach interface. The reflection from the package/bar interface is usually featureless and continuous in a part that has seen no thermal testing. The intensity from the bar/die attach interface is significantly stronger where the die attach is poor due to the reduced acoustic transmissivity. Comparison of this ratio to a threshold value based on a certain area fraction of good bonding will determine whether or not a part passes.

Also, this device may be useful for checking delamination at the package/bar interface in plastic packaged integrated circuits. This is a common mode of failure during thermal cycling, especially with large bars. When delamination occurs, the intensity of the package/bar reflection increases dramatically and the intensity of the bar/die attach interface goes to zero. A similar calibrated ratio test indicates the extent of delamination.

The intensity from the primary subsurface interface will pass through a minimum due to the cancellation of the reflection from the bonded area by the inverted reflection from the delaminated area. The primary subsurface interface is defined here as either the package/bar interface or the package/lead frame interface. The fraction of the total primary subsurface interface area that is delaminated can be determined by (1) taking the ratio of the amplitude of the primary subsurface interface area to the amplitude of a deeper interface reflection (such as the die attach interface reflection, for example); and (2), by measuring the general phase (i.e. inverted or non-inverted) of the primary subsurface interface reflection.

The technical advance represented by the invention as well as the objects thereof will become apparent from the following description of a preferred embodiment of the invention when considered in conjunction with the accompanying drawings, and the novel features set forth in the appended claims.

DESCRIPTION OF A PREFERRED EMBODIMENT

Figure 1:
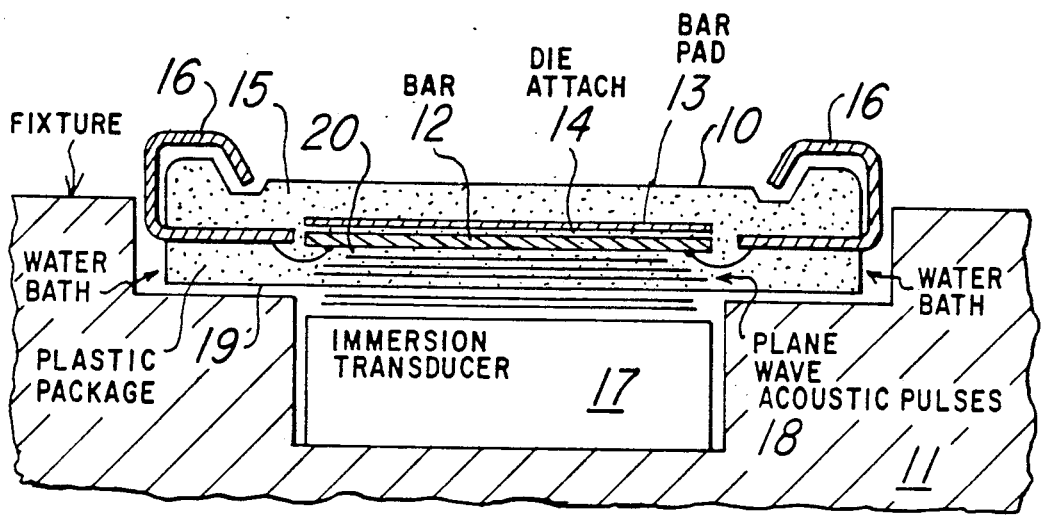
FIG. 1 illustrates the apparatus of the present invention as applied to plastic packaged integrated circuits using a permanent delay contact transducer.

FIG. 1 illustrates one configuration of the apparatus of the present invention using, for example, a water immersion transducer. The integrated circuit device, for example a plastic packaged integrated circuit, is inverted in fixture 11 so that the top of the package 19 is placed into the water bath with immersion transducer 17. Acoustic waves 18 are transmitted from transducer 17 through the water bath and plastic package 15 to the semiconductor bar 12. Bar 12 is attached at 14 to the lead frame bar pad 13. Each of the interface junctions will reflect waves back to the transducer 17.

There will be a reflection at the package interface 19, the semiconductor bar/package interface and the interface where the semiconductor bar 12 is attached to the bar pad 13.

Figure 2:
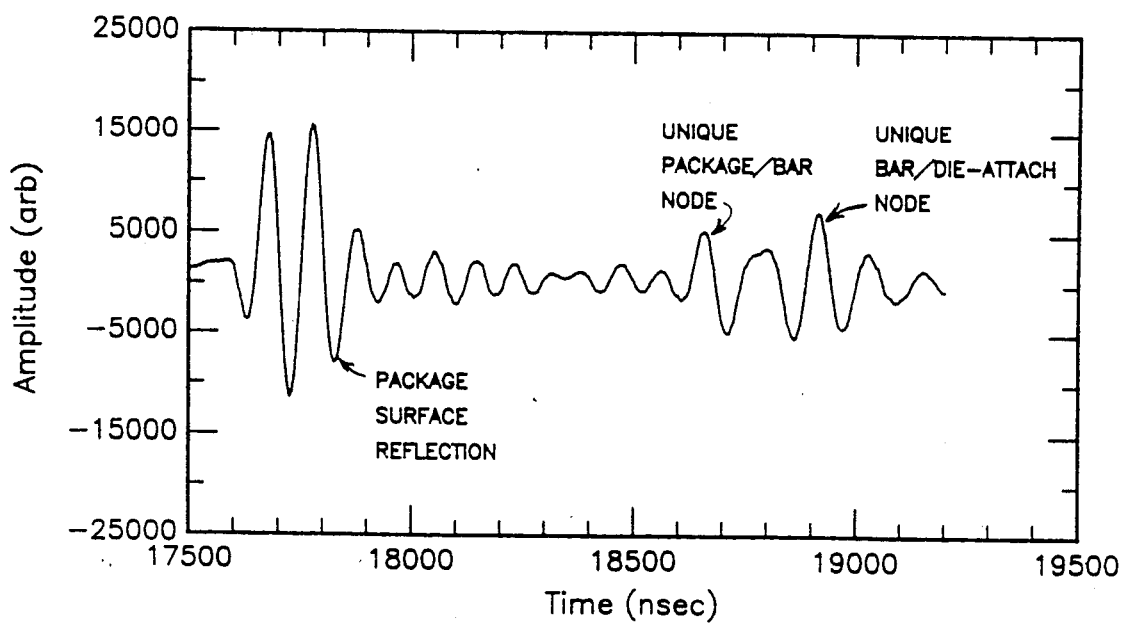
FIG. 2 shows the acoustic spectrum of a plastic package part taken over the semiconductor bar using a water immersion system.

FIG. 2 shows the portion of the acoustic pressure signal that includes the reflections from a plastic-packaged integrated circuit. The abscissa (Time(nsec)) is the time delay relative to the generation of the acoustic pulse at the transducer. The ordinate (Amplitude (arb)) is reflected pulse intensity in arbitrary units. The first pulse to arrive at the transducer between 17.5 and 18 microseconds delay is from the package surface. At about 1 microsecond later, the reflections from inside the package arrive at the transducer. These internal reflections are from interfaces such as the package/bar interface and the bar/die attach interface. In this particular figure (FIG. 2), a transducer center frequency of 10 MHz was used, and the package/bar and package/die attach interface reflections partially overlap in the time domain signal. The amplitudes of non-overlapping portions of these reflections are measured. The amplitudes are used to form a ratio for comparison with a threshold value to indicate the fraction of the total die attach area that is bonded.

Figure 3:
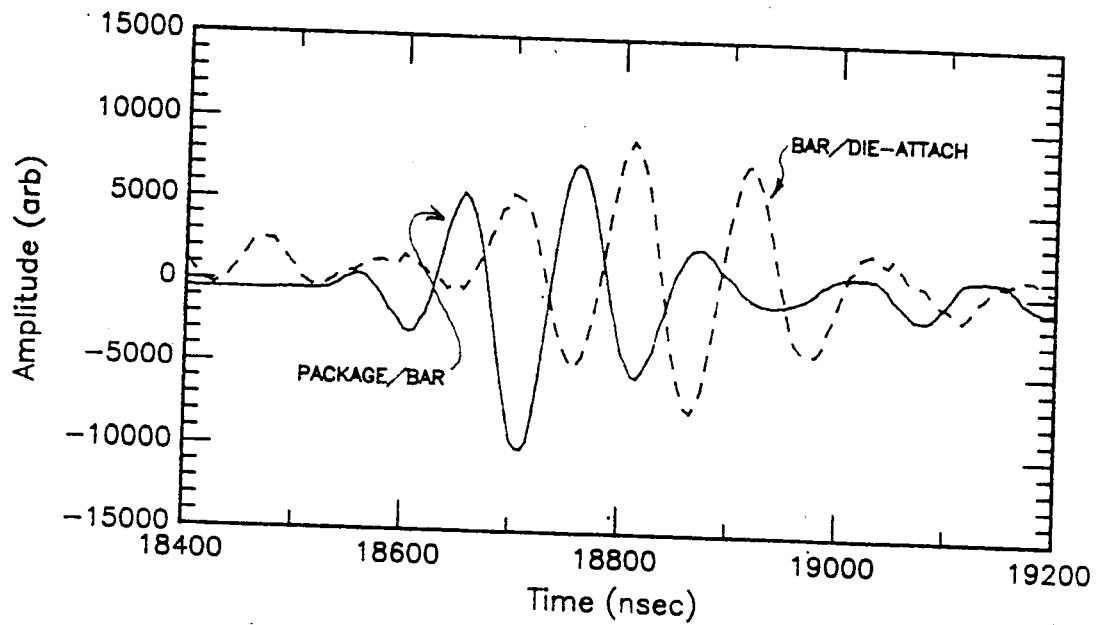
FIG. 3 shows the sub-surface portion of the spectrum of FIG. 2 and show the deconvoluted echoes from the package/bar interface and the bar/die interface.

The package/bar and bar/die attach interface reflections in FIG. 2 are shown separated in FIG. 3 with an expanded scale. This separation is performed by mathematical subtraction of an inverted copy of the acoustic pulse reflected from a delaminated portion of the package/bar interface.

Figure 4:
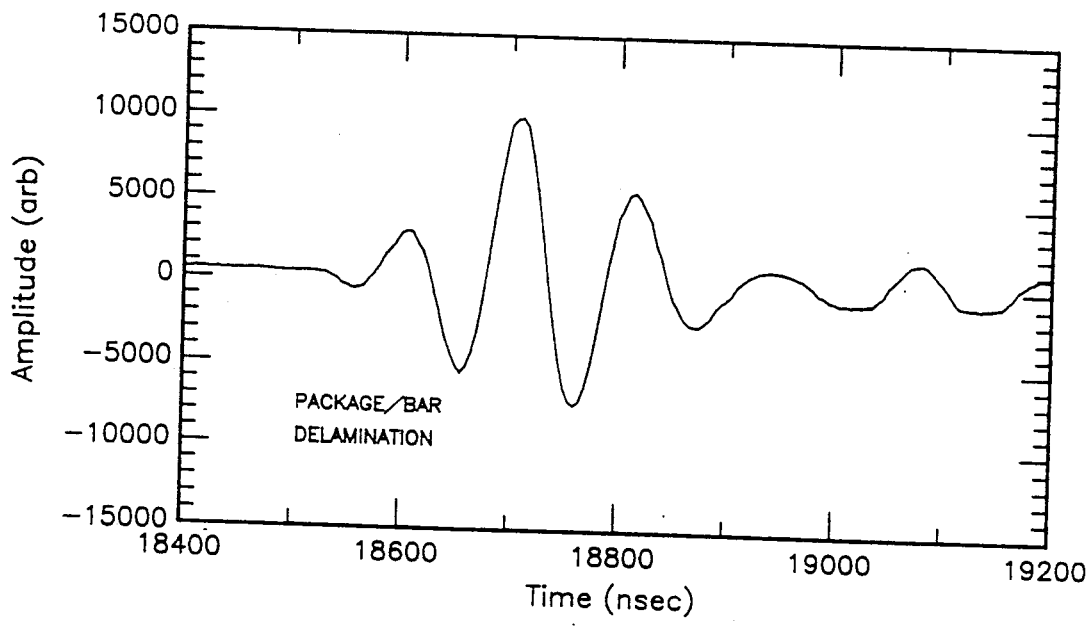
FIG. 4 shows a spectrum of a delaminated area.

This reflection from a delaminated portion of the package/bar interface is shown in FIG. 4. Note that this reflection is inverted, or 180 degrees out of phase with the reflection from a bonded portion of the package/bar interface. It should be noted that the reflections in FIG. 3 are completely temporarily resolved if a transducer of higher center frequency, such as 25 MHz is used.

It should also be noted that when the intensity of an interface reflection is measured, it is the absolute value, or rectified, intensity that is measured. This is a due to the inversion of the reflected pulse, for example, at a delaminated portion of the package/bar interface as compared to that from a bonded portion of the interface.

The application of this concept to determining die attach area in ceramic-packaged IC's is more straightforward. In the case of using a permanent delay contact transducer, ceramic-packaged parts are examined by placing the package on the solid delay line of the transducer right-side-up due to the air gap under the lid (FIG. 5).

Instead of a permanent delay contact transducer, a water immersion system can be used and the transducer can be above or below the IC package. The key reflections from a ceramic-packaged part are from the ceramic/bar interface and from the bar surface. The die attach adhesive transmits the acoustic signal very well where the bonding is good. These reflections are strong, well resolved and in a reciprocal relationship to each other.

Figure 5:
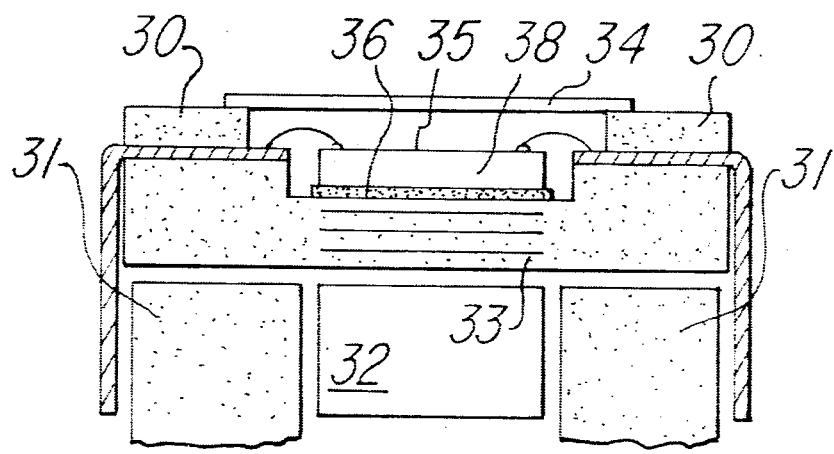
FIG. 5 illustrates the apparatus of the present invention as applied to ceramic packaged devices using a permanent delay contact transducer.

FIG. 5 illustrates apparatus used in testing ceramic dip packages using a permanent delay contact transducer, for example. Water immersion can also be used with ceramic packages. Device 30 resides on fixture 31 and over transducer 32. Acoustic waves 33 of between 5 and 100 MHz travel through the ceramic package to the ceramic/bar interface at 36 and through the semiconductor bar 38 to the bar surface 35. The device is enclosed with lid 34, but this part of the package has no affect on the test.

Figure 6:
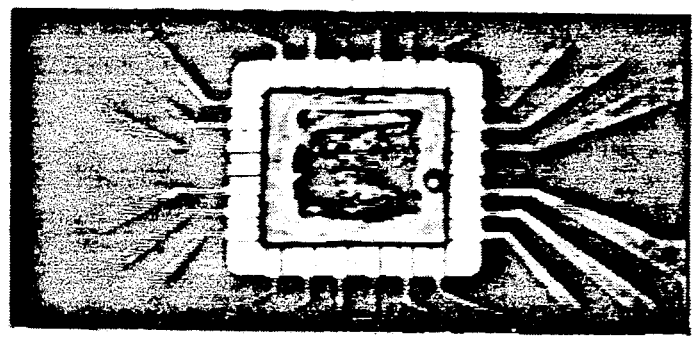
FIG. 6 is an acoustical image formed from reflections from several sub-surface interfaces in a ceramic package.

FIG. 6 shows an acoustic image formed from reflections from several sub-surface interfaces in a ceramic DIP using an acoustic microscope.

Figure 7:
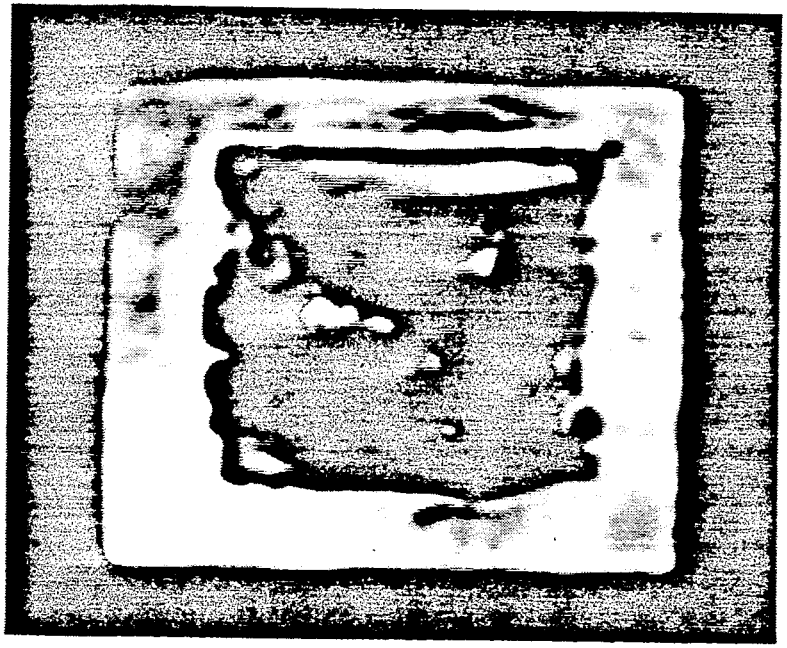
FIG. 7 is an image of the die attach area of the package of FIG. 6.

FIG. 7 is an image of the die attach area in FIG. 6. This image is formed from only the ceramic/bar reflection.

Figure 8:
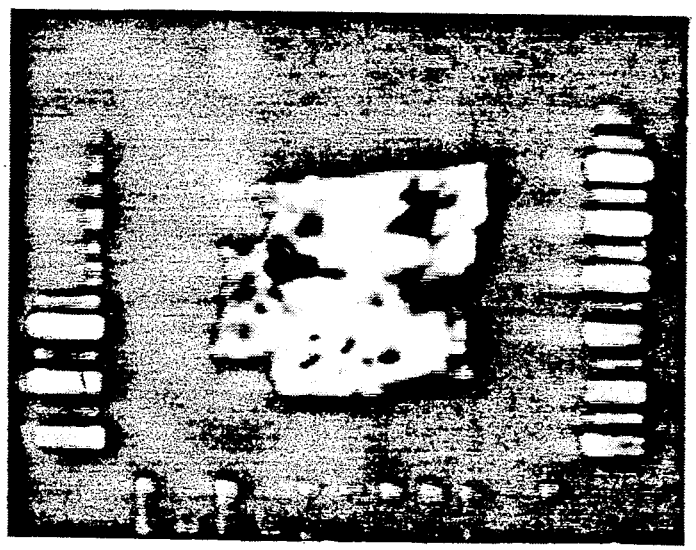
FIG. 8 is an acoustic image formed from only the depth of the bar surface in the ceramic package.

FIG. 8 is a similar image formed from only the bar surface depth. Note how one is the opposite of the other. The acoustic pulses transmitted through the well bonded areas are reflected at the bar surface. A ratio of the amplitudes of these two reflections will give a sensitive measure of average die attach area.

The apparatus illustrated in FIGS. 1 and 5 may be used in an automated production line. The devices to be tested may be transported to a position over the transducer and then moved as the next device to be test is brought into position, no operator is needed since the input and is totally automated. Each reading should be very fast, about 10 seconds per device.

The reflected pulse detector will automatically locate the appropriate reflections. In the case of a solid delay line, a coupling grease may be necessary. With the water path, nothing other than the water is needed.

What is claimed is:

1. A method for non-destructive measurement of die attach quality in plastic packaged integrated circuits using acoustic waves, comprising the steps of:
   contacting the integrated circuit with an acoustic delay/coupling medium;
   pulsing the integrated circuit with an acoustic wave through the delay/coupling medium;
   measuring the intensity of reflection of the pulse reflected from package/bar interface and from the bar/die attach interface;
   comparing the intensity of the reflection of the pulse reflected from the package/bar interface with the intensity of the pulse reflected from the bar/die attach interface to form a ratio; and
   comparing said ratio to a predetermined threshold value to determine the total bonded area at the bar/die attach interface.

2. The method according to claim 1, wherein said delay/coupling medium is water.

3. The method according to claim 1, including using said ratio to detect package/bar interface delamination.

4. The method according to claim 1, wherein said ratio is formed by convolving the intensity of the reflection of the package/bar interface and the intensity of the reflection of the bar/die attach interface.

5. The method according to claim 1, wherein said acoustic wave is 5 to 100 megahertz.

6. A method for non-destructive measurement of die attach quality in plastic packaged integrated circuits using acoustic waves, comprising the steps of:
   pulsing the integrated circuit with an acoustic wave to cause acoustical reflections from the package/bar interface and the bar/die attach interface within the integrated circuit package;
   measuring the intensity of the reflection from the package/bar interface and the intensity of the reflected wave from the bar/die attach interface;
   comparing the intensity of the reflection of the pulse reflected from the package/bar interface with the intensity of the pulse reflected from the bar/die attach interface to form a ratio; and
   comparing said ratio to a predetermined threshold value to determine the total bonded area at the bar/die attach interface.

7. The method according to claim 6, wherein an acoustic delay/coupling medium is used.

8. The method according to claim 6, including using said ratio to detect package/bar interface delamination.

9. The method according to claim 6, wherein said acoustic wave is 5-100 megahertz.

10. The method according to claim 6, wherein said integrated circuit is pulsed with a plane wave transducer.

11. The method according to claim 10, wherein said plane wave transducer is the same size as a semiconductor bar in the integrated circuit package.

12. An apparatus for non-destructive measurement of die attach quality in packaged integrated circuits using acoustic waves, comprising:
   a transducer for pulsing the integrated circuit with an acoustic wave to cause acoustical reflections from the package/bar interface and the bar/die attach interface within the integrated circuit package;
   a measuring circuit for measuring the intensity of the reflection from the package/bar interface and the intensity of the reflected wave from the bar/die attach interface;
   a first comparing circuit for comparing the intensity of the reflection of the pulse reflected form the package/bar interface with the intensity of the pulse reflected from the bar/die attach interface to form a ratio; and
   a second comparing circuit for comparing said ratio to a predetermined threshold value to determine the total bonded area at the bar/die attach interface.

13. The apparatus method according to claim 12, wherein a delay medium is used.

14. The apparatus according to claim 12, wherein said ratio is used to detect package/bar interface delamination.

15. The apparatus according to claim 12, wherein said ratio is formed by convolving the intensity of the reflection of the package/bar interface and the intensity of the reflection of the bar/die attach interface.

16. The apparatus according to claim 12, wherein the package under test is a plastic package.

17. The apparatus according to claim 12, wherein said acoustic wave is 5-100 megahertz.

18. The apparatus according to claim 12, wherein said integrated circuit is pulsed with a plane wave transducer.

19. The apparatus according to claim 12, wherein a plane wave transducer is the same size as a semiconductor bar in the integrated circuit package.

20. The method according to claim 1, wherein the acoustic wave is transmitted through an aperture to adjust the size and shape of the transducer sound field.

21. The method according to claim 6, wherein the acoustic wave is transmitted through an aperture to adjust the size and shape of the transducer sound field.

22. The apparatus according to claim 12, including a aperture through which the acoustic wave is transmitted to adjust the size and shape of the transducer sound field.

23. The apparatus according to claim 12, wherein the transducer is a scanned array transducer.

24. A method for non-destructive measurement of die attach quality in ceramic packaged integrated circuits using acoustic waves, comprising the steps of:
   (a) pulsing the integrated circuit with an acoustic wave produced by a transducer;
   (b) measuring the intensity of reflections from the die-attach interface and the bar surface;
   (c) comparing the intensity of the pulse reflected from the die-attach interface with the bar surface reflection to form a ratio; and
   (d) comparing said ratio to a predetermined threshold value to determine the total bonded area at the bar/die attach interface.

25. The method of claim 24 wherein the transducer is a permanent delay contact transducer.

26. The method of claim 24 wherein the transducer is acoustically coupled to the integrated circuit through water.

27. The method of claim 24 wherein the transducer is positioned above the integrated circuit.

28. The method of claim 24 wherein the transducer is a plane wave transducer.

29. The method of claim 28 wherein the plane wave transducer is the same size as a semiconductor bar in the integrated circuit.

* * * * *